US012636019B2

(12) United States Patent
Abboud

(10) Patent No.: US 12,636,019 B2
(45) Date of Patent: May 26, 2026

(54) BONE DRILL BIT AND HANDPIECE FOR USING THE BONE DRILL BIT

(71) Applicant: Marcus Abboud, Setauket, NY (US)

(72) Inventor: Marcus Abboud, Setauket, NY (US)

( * ) Notice: Subject to any disclaimer, the term of this patent is extended or adjusted under 35 U.S.C. 154(b) by 0 days.

(21) Appl. No.: 16/770,630

(22) PCT Filed: Dec. 8, 2017

(86) PCT No.: PCT/EP2017/082009
§ 371 (c)(1),
(2) Date: Jun. 8, 2020

(87) PCT Pub. No.: WO2019/110119
PCT Pub. Date: Jun. 13, 2019

(65) Prior Publication Data
US 2020/0367992 A1    Nov. 26, 2020

(51) Int. Cl.
*A61B 17/16*       (2006.01)
*A61C 3/02*        (2006.01)
*A61B 17/00*       (2006.01)
*A61B 90/92*       (2016.01)

(52) U.S. Cl.
CPC ............ *A61B 17/1673* (2013.01); *A61C 3/02* (2013.01); *A61B 2017/00084* (2013.01); *A61B 90/92* (2016.02)

(58) Field of Classification Search
CPC .................. A61C 3/02; A61C 2201/00; A61B 2017/0084; A61B 17/1615
See application file for complete search history.

(56) References Cited

U.S. PATENT DOCUMENTS

| | | | | |
|---|---|---|---|---|
| 4,156,365 A | * | 5/1979 | Heinmets | ........... A47G 19/2227 |
| | | | | 374/E11.018 |
| 5,078,605 A | * | 1/1992 | Sutter | .................. B23Q 1/0036 |
| | | | | 433/104 |
| 5,354,200 A | | 10/1994 | Klein et al. | |
| 5,918,981 A | * | 7/1999 | Ribi | ....................... G01K 13/00 |
| | | | | 374/162 |
| 2003/0036747 A1 | | 2/2003 | Mc Ie et al. | |
| 2007/0293867 A1 | * | 12/2007 | Anitua | ................. A61C 8/0089 |
| | | | | 606/80 |
| 2009/0128330 A1 | | 5/2009 | Monroe | |

(Continued)

FOREIGN PATENT DOCUMENTS

| | | | | |
|---|---|---|---|---|
| CN | 105751387 A | * | 7/2016 | ............. B28B 1/146 |
| DE | 20 2004 002 472 U1 | | 4/2004 | |

(Continued)

OTHER PUBLICATIONS

Machine translation of DE202004002472U1, retrieved from https://worldwide.espacenet.com/patent/search/family/032240852/publication/DE202004002472U1?q=de202004002472 (Year: 2004).*

(Continued)

*Primary Examiner* — Heidi M Eide
(74) *Attorney, Agent, or Firm* — CM Law LLP; Robert C. Klinger

(57) ABSTRACT

A bone drill bit includes a metal drill shaft body. The metal drill shaft body includes a drilling section, a clamping section, and a passive temperature-sensitive optical indicator which is in a thermo-conducting connection to the metal drill shaft body.

11 Claims, 2 Drawing Sheets

(56)           References Cited

U.S. PATENT DOCUMENTS

| | | | |
|---|---|---|---|
| 2009/0211421 A1* | 8/2009 | Lier | B23D 61/026 |
| | | | 83/522.27 |
| 2009/0236109 A1* | 9/2009 | Wu | B25F 5/02 |
| | | | 374/E1.002 |
| 2013/0344458 A1* | 12/2013 | Taha | A61C 8/0022 |
| | | | 433/174 |
| 2015/0003496 A1* | 1/2015 | Willing | G01K 13/08 |
| | | | 374/161 |
| 2016/0051283 A1 | 2/2016 | Runden et al. | |
| 2017/0095261 A1 | 4/2017 | Strbac et al. | |
| 2018/0243873 A1* | 8/2018 | Yamamoto | B23Q 17/0995 |
| 2018/0263725 A1* | 9/2018 | Pesach | A61B 34/20 |
| 2019/0300740 A1* | 10/2019 | Aida | G01K 11/12 |

FOREIGN PATENT DOCUMENTS

| | | | |
|---|---|---|---|
| WO | WO 2007/006698 A1 | 1/2007 | |
| WO | WO 2007/090387 A2 | 8/2007 | |
| WO | WO 2015/172174 A2 | 11/2015 | |

OTHER PUBLICATIONS

Visible colors retrieved from https://www.britannica.com/science/color/The-visible-spectrumd (Year: 2022).*

* cited by examiner

BONE DRILL BIT AND HANDPIECE FOR USING THE BONE DRILL BIT

CROSS REFERENCE TO PRIOR APPLICATIONS

This application is a U.S. National Phase application under 35 U.S.C. § 371 of International Application No. PCT/EP2017/082009, filed on Dec. 8, 2017. The International Application was published in English on Jun. 13, 2019 as WO 2019/110119 A1 under PCT Article 21(2).

FIELD

The present invention relates to a medical bone drill bit for drilling a hole into a bone of a patient, preferably into a jaw bone of a patient.

BACKGROUND

The process of drilling a hole into a patient's bone, for example for preparing a dental implant bed, is very sensitive with respect to the temperatures appearing at the bone of the patient during the drilling action. If the patient's bone is damaged because of too high local temperatures during the drilling action, the following implanting and healing process is significantly complicated.

To avoid a temperature-caused damage of the bone, local bone temperatures of more than 47° C. for more than 30 to 60 seconds must be avoided.

A direct temperature measurement at the patient's bone is difficult to provide. WO 2015 172 174 A1 describes to provide a drill bit with an integrated miniaturized temperature sensor. But it is not described in this document how to energize the rotating sensor and how to transmit the sensor's temperature information from the rotating drill bit to the non-rotating handpiece.

SUMMARY

An aspect of the invention to provide a bone drill bit allowing the drilling person to have a temperature indication during the drilling action.

In an embodiment, the present invention provides a bone drill bit which includes a metal drill shaft body. The metal drill shaft body includes a drilling section, a clamping section, and a passive temperature-sensitive optical indicator which is in a thermo-conducting connection to the metal drill shaft body.

BRIEF DESCRIPTION OF THE DRAWINGS

The present invention is described in greater detail below on the basis of embodiments and of the drawings in which.

DETAILED DESCRIPTION

Figure 1:
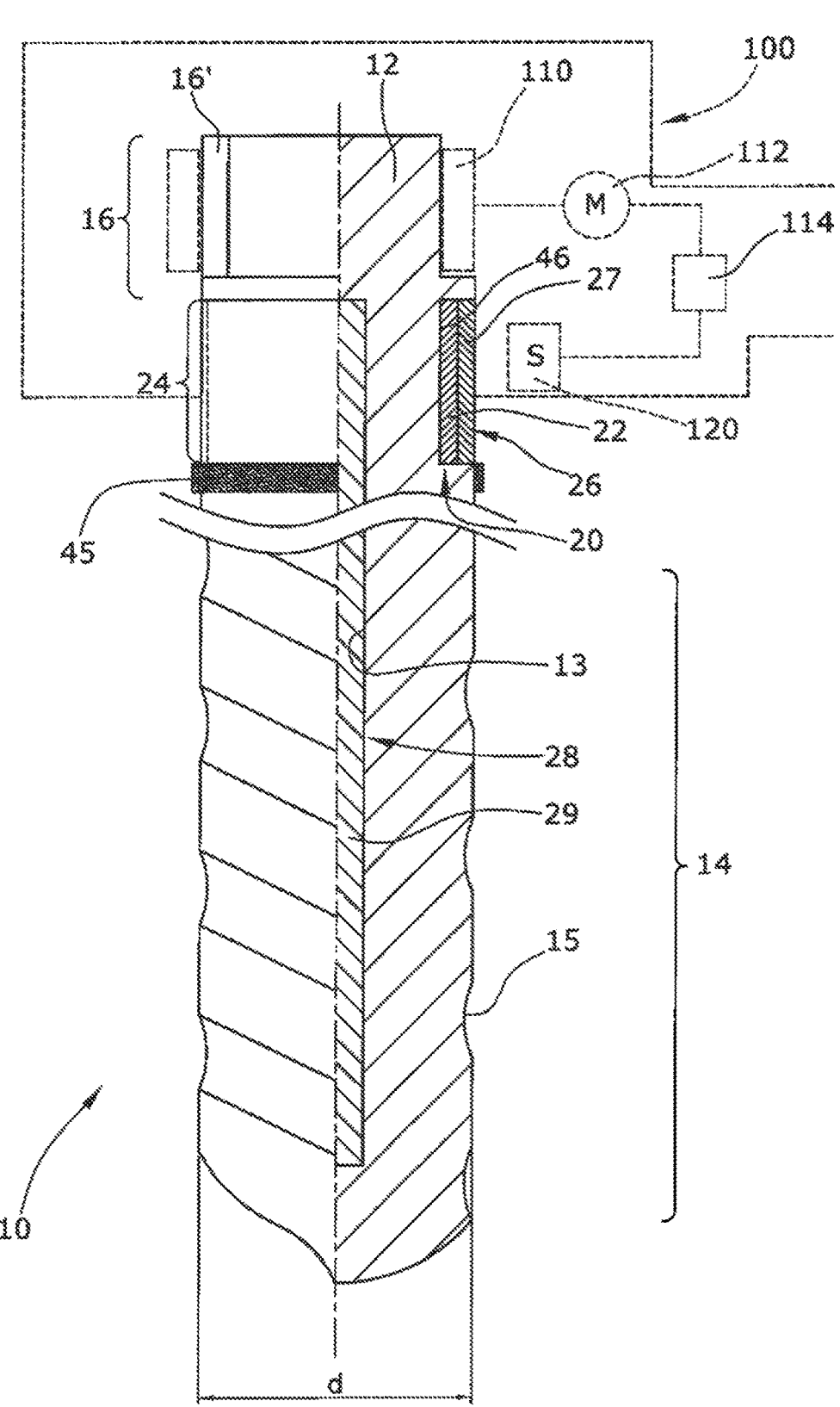
FIG. 1 shows a bone drill bit according to the invention together with a handpiece holding the drill bit.

The bone drill bit according to the invention is preferably a dental bone drill bit, and is provided with a metal drill shaft body being provided, seen in longitudinal direction, with a drilling section defined by a distal shaft section which is provided with cutting edges and a clamping section at the proximal drill bit end provided with a clamping surface where the drill bit is clamped by clamping means of a handpiece.

The drill shaft body is provided with a passive temperature-sensitive optical indicator which is fixed to the metal drill shaft body in a thermo-conducting manner. The term 'passive' in this context means that the indicator does not provide an electrical signal which could be evaluated electrically. The term 'thermo-conducting' in this context means that no thermo-insulating layer, for example no layer comprising a substantive volumetric share of air, is provided between the optical indicator and the metal drill shaft body.

The indicator shows different colors, preferably colors visible for a human being, which indicate different temperatures. The indicator's color-change can be somehow proportional to the corresponding temperature-change. Alternatively and preferably, the color change characteristics of the indicator can be dramatic around the critical temperature in a relatively small defined temperature interval of a few Kelvin, whereas, above and below this defined and relatively small temperature interval, the indicator color does not substantially change with the drill bit body temperature.

The color-changing property of the indicator can be reversible or, alternatively, can be irreversible. If the color changing property of the indicator is irreversible, the indicator allows to record and to prove that a particular and defined temperature limit has not been exceeded during the complete drilling operation. If the color-changing property of the indicator is reversible, the drill bit can be used a couple of times for a couple of bone drilling procedures.

The drill shaft body of the bone drill bit is generally made of 'medical steel' which is basically an inert, non-corrosive and sufficiently hard steel. Medical steel generally has a relatively good and high temperature conductivity so that the heat at the distal drilling section of the drill shaft body is heat conducted relatively quickly in longitudinal direction through the drill shaft body to the proximal end section of the drill bit. The temperature-sensitive optical indicator is provided proximately of the drilling section so that the temperature information is somehow visible at the proximal end section of the bone drill bit. The temperature-sensitive optical indicator allows to relativity simply provide a visible or optically detectable indication about the temperature at the drill section of the bone drill bit.

Preferably, the temperature-sensitive optical indicator is defined by a color-changing substance changing its visible-spectrum color depending on the temperature of the drill shaft body. The term 'visible-spectrum' in this context means that the color of the color-changing indicator substance is visible for a human being. As a result, the person providing the drilling action is able to see and to watch the color shift of the indicator and, therefore, is able to see if the indicator color changes to a color which indicates an exceed of the medically allowed maximum temperature at the drill section of the bone drill bit.

Preferably, a reference color area can be provided next to or directly adjacent to the temperature-sensitive optical indicator to facilitate the human detection and evaluation of the color of the optical indicator. The reference color area can have the color of the optical indicator indicating an exceeding temperature or, alternatively, can have the color of the optical indicator indicating an allowed temperature.

According to a preferred embodiment, the temperature-sensitive optical indicator is defined by a visible indicator ring being provided around the drill shaft body. More preferably, the optical indicator is located axially between the drilling section and the clamping section of the drill shaft body. The ring-like indicator ring is visible which means that the indicator ring does not dive into the drill hole during the drilling operation and is not clamped by a clamping means. Preferably, the term 'visible' in this context means that the ring is generally visible during the drilling action for the person providing the drilling action.

Generally, the optical indicator ring is applied to the drill shaft body during the manufacturing process of the bone drill bit. Alternatively, the optical indicator ring can be provided separately, and can be manually applied to the drill shaft body by simply shifting the indicator ring over the drill shaft body. This could be done by the person providing the drilling action.

Alternatively or additionally, the temperature-sensitive optical indicator is located at the proximal end surface of the drill shaft body. Some handpieces of some manufacturers allow to see the proximal end surface of the clamped drill shaft body so that the optical indicator located at the proximal end surface is easily visible during the drilling action for a person providing the drilling action.

Preferably, the temperature-sensitive optical indicator is covered by a temperature-isolating and visually transparent protection shielding. The protection shielding thermally isolates the optical indicator so that a cooling liquid which can be present at the outside surface of the bone drill bit during the drilling action does not significantly cool down the temperature-sensitive optical indicator. Additionally, the protection shielding protects the optical indicator mechanically. The protection shielding is transparent so that the optical indicator is visible through the protection shielding.

According to a preferred embodiment, a separate heat conductor is provided within the drill shaft body. The heat conductor is at least in part axially overlapping with the drilling section and with the temperature-sensitive indicator. The temperature conductivity of the heat conductor is higher than the temperature conductivity of the drill shaft body. The heat conductor improves the conductive heat transfer from the drilling section to the temperature-sensitive optical indicator so that the temperature at the optical indicator correlates more with the temperature of the drill shaft body at the drill section and the temperature adaption delay is reduced significantly.

Preferably, the heat conductor is provided with a longitudinal conductor pin located in a central cylindrical conductor bore in the drill shaft body. The conductor pin defines the core of the bone drill bit over a substantial length of the bone drill bit.

According to a preferred embodiment of the invention, the color-changing substance changes its color by more than 30 nm at an indicator temperature shift from 37° C. to 42° C. The color-changing substance is provided with suitable color changing particles and can thereby be defined to show a strong color changing behavior when the temperature arrives at 42° C.

Preferably, the drill bit is for dental applications and the maximum outside diameter of the drill shaft body is less than 5 mm. Dental bone drill bits are very compact and small in diameter so that it is very difficult to provide an electronic temperature sensor within the drill body. Providing a passive temperature-sensitive optical indicator at the outside surface of the bone drill bit avoids any mechanical weakening of the drill shaft body.

According to another concept of the invention, a handpiece with a clamping arrangement for clamping the bone drill bit according to one of claims 1 to 10 is provided. The handpiece is provided with a static, non-rotating color detection means for detecting the color of the passive temperature-sensitive indicator at the rotating bone drill bit. In other words, the color of the optical indicator is detected by a color detection means, which is a color sensor providing an electrical signal. The color detection means allows, for example, to stop or to decelerate the rotation of the bone drill bit if the optical indicator indicates a critical shaft body temperature.

Two embodiments of the invention are explained with reference to the enclosed drawings.

Figure 2:
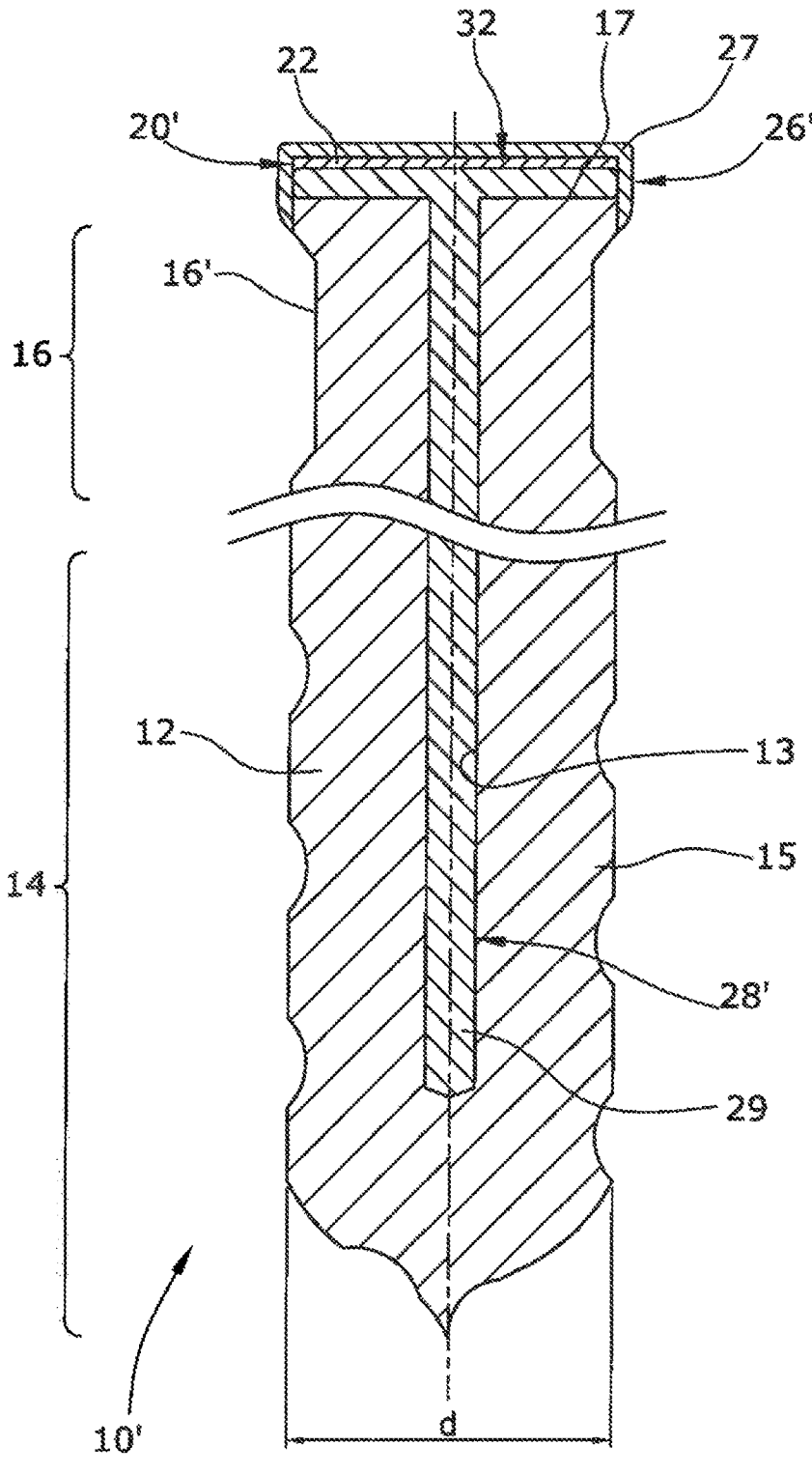
FIG. 2 shows a second embodiment of a bone drill bit according to the invention.

FIG. 1 and FIG. 2 both show a bone drill bit 10; 10' for dental applications. The bone drill bit 10 of FIG. 1 is provided with a drill shaft body 12 made out of medical steel. Seen in longitudinal direction, the bone drill bit 10 has a distal drill section 14, a proximal clamping section 16 and is provided with a temperature-sensitive optical indicator 20 between the sections 14,16. The drill shaft body 12 is provided with a helical flute 15 which defines the drill section 14. The drill shaft body 12 is provided with a clamping surface 16' at the clamping section 16. The clamping surface 16' can be, seen in cross section, of circular or polygonal shape. The maximum diameter d of the drill shaft body 12 is 5.0 mm.

The temperature-sensitive optical indicator 20 is provided as a visible indicator ring 24 being in a direct and heat-conductive connection to the drill shaft body 12. The visible indicator ring 24 is embedded in a circular ring-like recess 46 and is covered with a transparent, temperature-isolating and ring-like protection shielding 26 completely covering the optical indicator 20. The protection shielding 26 can be defined by a suitable transparent plastic material body 27.

The optical indicator 20 is defined by a color changing substance 22 having a reversible or, alternatively, irreversible color changing behavior. The visible-spectrum color of the color-changing substance 22 changes its color with at least 30 nm at a temperature shift from 39° C. to 42° C. The color-changing substance can be any suitable thermochromatic substance, for example a substance comprising liquid crystals and/or leuco dyes.

A ring-like reference color area 45 is provided distally directly adjacent to the optical indicator 20. If the indicator 20 and the reference color area 45 are not covered by a handpiece, the reference color area 45 facilitates to the person providing the drilling action to optically detect a relevant color change of the optical indicator 20 by comparing the colors of the optical indicator 20 and the reference color area 45.

The drill shaft body 12 is provided with a central axial conductor bore 13 which is completely filled with a heat conductor pin 29 defining a heat conductor 28. The heat conductor 28 is made of a material having a better thermal conductivity than the medical steel of the drill shaft body 12. The heat conductor 28, seen in longitudinal direction, substantially overlaps the drill section 14 and the optical indicator 20. The heat conductor 28 can, for example, be made of copper or Tungsten.

The drill bit 10 is clamped and engaged in a hand piece 100 which is provided with a clamping means 110 holding and engaging the clamping section 16 of the drill shaft body 12. The clamping means 110 is rotated and driven by a drill machine motor 112. The drill machine handpiece 100 of this embodiment is also provided with a color detection means 120 which is a color sensor and is also provided with a light emitter illuminating the rotating optical indicator 20. The color detection means 120 can 'see' the rotating optical indicator 20 so that the indicator color indicating the temperature of the drill shaft body 12 at the drill section 14 can indirectly be detected by the color detection means 120. The handpiece 100 is also provided with a control device 114 which can reduce the rotational speed of the drill machine motor 112 if the detected temperature should exceed a maximum defined maximum temperature.

Alternatively, the handpiece could be designed to allow a person to see the optical indicator 20 during the drilling action so that the person providing the drilling action can see by himself if the optical indicator 20 indicates a critical temperature.

FIG. 2 shows an alternative embodiment of the bone drill bit 10'. In contrast to the bone drill bit 10 of FIG. 1, the bone drill bit 10' of FIG. 2 is provided with the temperature-sensitive optical indicator 20' at the proximal end surface 17 of the drill shaft body 12. The heat conductor 28' is provided with a longitudinal conductor pin 29 located in the central conductor bore 13 and is also provided with a proximal disk body 32 directly being in contact with the proximal end surface 17 of the drill shaft body 12. The proximal surface of the heat conductor disk body 32 is coated with the temperature-sensitive optical indicator 20' which also has a corresponding disk-like shape. The complete drill bit head portion is coated with a cup-shaped heat insulating protection shielding 26'.

The present invention is not limited to embodiments described herein; reference should be had to the appended claims.

What is claimed is:

1. A medical bone drill bit comprising:
a metal drill shaft body configured to extend from a drilling device for drilling into living bone, the metal drill shaft body comprising a drilling section at a distal end, a clamping section at a proximal end, and a passive heat-sensitive non-numeric optical indicator, defined by a color-changing substance which changes a visible-spectrum color depending on amount of heat sensed, wherein the color changing substance changes color by more than 30 nm in the visible spectrum when a temperature shift from 40° C. to 47° C. of the metal drill shaft body occurs, the passive heat-sensitive non-numeric optical indicator is fixed to the metal drill shaft body so as to be visible to a user as the drill bit is in use on living bone, the passive heat-sensitive non-numeric optical indicator is coupled to a thermal-conducting conductor that extends from the drilling section through the metal drill shaft body when the bone drill bit is drilling into living bone, such that the passive heat-sensitive non-numeric-optical indicator changes its indication based on a change in an amount of heat at the drill bit distal end created by friction between the drill bit and living bone, so as to provide a non-numeric warning of excessive heat on the living bone during use, the metal drill shaft body comprising a reference color area adjacent to the passive heat-sensitive non-numeric optical indicator and configured to facilitate human detection and evaluation of the color of the passive heat-sensitive non-numeric-optical indicator.

2. The bone drill bit as recited in claim 1, wherein the passive heat-sensitive non-numeric optical indicator is provided as an indicator ring which is arranged around the metal drill shaft body.

3. The bone drill bit as recited in claim 1, wherein the passive heat-sensitive non-numeric optical indicator is arranged axially between the drilling section and the clamping section.

4. The bone drill bit as recited in claim 1, wherein the passive heat-sensitive non-numeric optical indicator is arranged at the proximal end of the metal drill shaft body.

5. The bone drill bit as recited in claim 1, wherein the passive heat-sensitive non-numeric optical indicator is covered by a protection shielding which is heat insulating and transparent.

6. The bone drill bit as recited in claim 1, wherein the thermal-conducting
conductor is arranged within the metal drill shaft body and to at least partially axially overlap with the drilling section and the passive heat-sensitive non-numeric optical indicator, wherein, a heat conductivity of the thermal-conducting conductor is higher than a heat conductivity of the metal drill shaft body.

7. The bone drill as recited in claim 6, wherein, the metal drill shaft body further comprises a central conductor bore, and the thermal-conducting conductor comprises a longitudinal conductor pin which is arranged in the central conductor bore in the metal drill shaft body.

8. The bone drill bit as recited in claim 1, wherein a maximum outside diameter of the metal drill shaft body is less than 5 mm so that the bone drill bit is usable for a dental application.

9. The bone drill bit as recited in claim 1 wherein the reference color area has a color indicative of a temperature the bone drill bit exceeding a predetermined temperature.

10. The bone drill bit as recited in claim 1 wherein the reference color area has a color indicative of the bone drill bit having an allowed temperature.

11. A system comprising:
a bone drill bit as recited in claim 1;
a handpiece coupled to the bone drill bit: and a static color detector configured to detect a color of the passive heat-sensitive non-numeric optical indicator when the bone drill bit rotates.

* * * * *